United States Patent [19]

Barber et al.

[11] Patent Number: 5,245,191
[45] Date of Patent: Sep. 14, 1993

[54] SEMICONDUCTOR SENSOR FOR GAMMA-RAY TOMOGRAPHIC IMAGING SYSTEM

[75] Inventors: Herbert B. Barber; Harrison H. Barrett; Eustace L. Dereniak; Michel M. Rogulski, all of Tucson, Ariz.

[73] Assignee: The Board of Regents of the University of Arizona, Tucson, Ariz.

[21] Appl. No.: 868,181

[22] Filed: Apr. 14, 1992

[51] Int. Cl.⁵ ............................ G01T 1/161; G01T 1/24
[52] U.S. Cl. ............................ 250/363.04; 250/363.10; 250/370.09
[58] Field of Search ............ 250/363.04, 363.06, 250/363.07, 370.08, 370.09, 370.10, 370.12, 370.13, 363.10

[56] References Cited

U.S. PATENT DOCUMENTS

| | | | |
|---|---|---|---|
| 3,825,757 | 7/1974 | Barrett | 250/363 |
| 3,961,191 | 6/1976 | Stoner et al. | 250/312 |
| 4,092,540 | 5/1978 | Barrett | 250/363 |
| 4,165,462 | 8/1979 | Macovski et al. | 250/363.06 X |
| 4,514,632 | 4/1985 | Barrett | 250/368 |
| 4,734,588 | 3/1988 | Akai | 250/370.09 |
| 4,879,464 | 11/1989 | Iinuma | 250/361 |
| 4,905,265 | 2/1990 | Cox et al. | 250/370.09 X |

OTHER PUBLICATIONS

Mochiki et al., "Amorphous Silicon Position-Sensitive Detector," Nuclear Instruments and Methods in Physics Research A273, 1988, pp. 640-644.

Iwanczyk, J. S. et al., "Development of Mercuric Iodide Energy Dispersive X-Ray Array Detectors," IEEE Transactions on Nuclear Science, vol. 35, No. 1, Feb. 1988, 93-97.

Audet, S. A. and S. E. Wouters, "Monolithic Integration of a Nuclear Radiation Sensor and Transistors on High-Purity Silicone," IEEE Transactions on Nuclear Science, vol. 37, No. 1, Feb. 1990, 15-20.

Cho, G. et al., "Assessment of TFT Amplifiers for a-Si:H Pixel Particle Detectors," IEEE Transactions on Nuclear Science, vol. 37, No. 3, Jun. 1990, 1142-1148.

Gaalema, IEEE Transactions on Nuclear Science, vol. NS-32, No. 1, Feb. 1985, p. 417.

*Primary Examiner*—Constantine Hannaher
*Assistant Examiner*—Edward J. Glick
*Attorney, Agent, or Firm*—Antonio R. Durando; Harry M. Weiss

[57] ABSTRACT

A hybrid gamma-ray semiconductor detector is used in combination with attenuating apertures of the kind used in emission computed tomography. The detector comprises a slab of semiconductor material partitioned into multiple cells individually connected to a multiplexer through indium-bump pressure welds for the sequential read-out of integrated pulses generated in each cell as a result of gamma-ray absorption events. The single output channel provided by the multiplexer permits the construction of semiconductor sensor cells approximately one millimeter in size for improved spatial resolution of the detector. The greater resolution of the detector makes it possible to narrow the distance between the image forming apertures and the detector's surface, thus minimizing overlapping of the gamma-ray radiation and the size of the overall apparatus. As a result of the smaller acceptable distance between the aperture surface and the detector, it is also possible to have a greater number of apertures without overlap with a resulting substantial improvement in system sensitivity.

17 Claims, 3 Drawing Sheets

Fig. 13c
Connections to Multiplexer

Fig. 13d
Connections to PC Board

Fig. 14

SEMICONDUCTOR SENSOR FOR GAMMA-RAY TOMOGRAPHIC IMAGING SYSTEM

BACKGROUND OF THE INVENTION

1. Field of the Invention

This invention is related to the general field of radiation imaging for medical applications. In particular, the invention provides a new method and apparatus for detecting radiation emitted from an object under examination in order to construct an image corresponding to the spatial distribution of the source of radiation within the object.

2. Description of the Prior Art

The goal of medical imaging is to provide a spatial mapping of some parameter, feature, or process within a biological entity. Generally speaking, two broad categories of medical imaging systems exist: those that provide anatomical information and those that produce a functional mapping of the object under observation. Emission imaging (or nuclear medicine) comprises a class of imaging techniques that fall in the second category.

In its simplest form, an apparatus that can be used to make such a spatial mapping consists of an x-ray source that generates a collimated beam of x rays in the direction of the object under observation and a suitable detector that measures the intensity of the incident x-ray beam after it has passed through the object (transmission computed tomography). The sensor detects and measures the information required to produce an image representing the attenuation of the radiation resulting from the differential absorption and scattering caused by the structure through which the beam traveled.

More complex techniques used in nuclear medicine involve the injection of a radioactive substance into a patient's body and the measurement of the emitted radiation (gamma rays), viewed through a system of apertures in an impermeable medium, by radiation sensitive detectors. Typically, before injection the radioactive tracer (radionuclide) is combined with a substance that is known to be preferentially concentrated in the organ of interest, so that the preferential absorption of the resulting radiopharmaceutical will correspond to an indication of blood flow, metabolism, or receptor density within the organ. Thus, an image of the resulting radioactive distribution within the organ of interest will yield functional information about the organ. Either a single projection image of the emission distribution may be taken (planar imaging) or many projection images may be acquired from different directions and used to compute the three dimensional emission distribution (single photon emission computed tomography, or SPECT).

Another technique in nuclear medicine, called positron emission tomography (PET), utilizes positron-emitting radionuclides and detects two gamma rays from individual positron annihilations using coincidence timing techniques. The scope of this disclosure is limited to single-photon techniques such as planar imaging and SPECT.

Since photons in the energy range used in nuclear medicine are not easily refracted or reflected, data are collected by placing attenuating apertures between the patient and the detector plane, so that each detector has an associated field of view defined by the aperture. Photons that are recorded by a particular detector element in the detector plane are known to have originated in a certain small portion of the object space. The number of photons detected by a given detector is proportional to a weighted integral of the activity contained in the region it sees. By utilizing the information collected by many detector elements or cells, each viewing different but overlapping regions of the object space, an estimate of the original activity distribution can be produced by a reconstruction algorithm according to analytical methods and techniques that are well understood by those skilled in the art.

Figure 1:
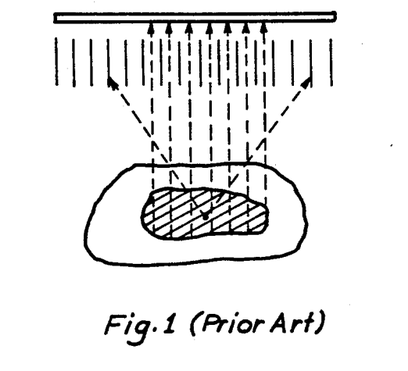
FIG. 1a is schematic representation of the structure and function of a parallel-hole collimator.

Different kinds of apertures are commonly used to provide the desired select field of view. For example, FIG. 1 shows a parallel-hole collimator that consists of a thick attenuator (usually lead) through which a large number of closely packed, parallel, holes exist. The collimator is positioned between the object under observation and the detector in such a way that each detector element views a region of the object space through a portion of the collimator. Thus, the region that each detector element sees is, to a first approximation, defined by multiple parallel straight lines through the object.

Figure 2:
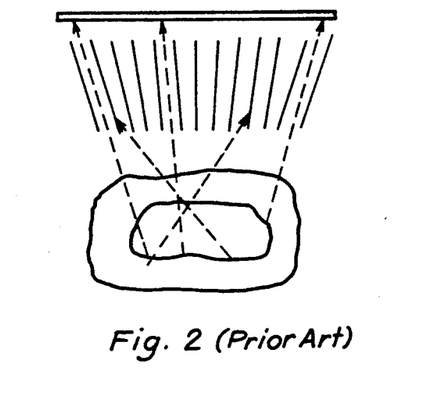
FIG. 2 is a schematic representation of the structure and function of a focussed collimator.

The focussed collimator shown in FIG. 2 is similar to the parallel-hole collimator, but the holes are oriented so that they point to a single focal point. If the focus is on the front side of the detector, as illustrated in the figure, the collimator magnifies the region of interest, which has the effect of distributing the projection of the object over more detector elements, which in turn permits the efficient use of a large detector when viewing small objects. If, on the other hand, the holes focus to a point behind the detector (not illustrated in the figure), the projection of the object is obviously reduced (minification). This type of collimator is used to project a large object onto a small detector surface.

Figure 3:
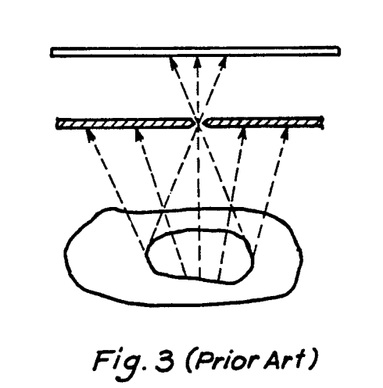
FIG. 3 is a schematic representation of the structure and function of a pinhole aperture.

The aperture depicted in FIG. 3 consists of a pinhole in an attenuator. The ideal pinhole, which is infinitesimally small, defines a bundle of rays that are emitted from the object and converge to a point on the aperture surface. After passing through the pinhole, the rays diverge and strike different detector elements. Therefore, just as in the case of a collimator, each detector element in an ideal pinhole imaging system receives radiation from a single line through the object. A pinhole aperture can also be used to magnify or minify an object by varying its position relative to the object and the detector locations. For a fixed object-to-detector distance, moving the pinhole closer to the object will magnify the projection of the object onto the detector plane, while moving the pinhole closer to the detector will reduce the projected image.

Figure 4:
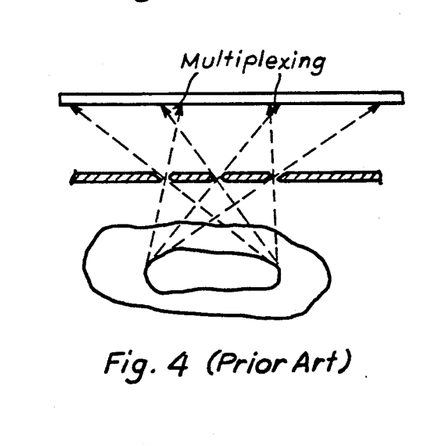
FIG. 4 is a schematic representation of the structure and function of a multiple-pinhole coded aperture illustrating the overlapping of signals received through the apertures.

Apertures can consist of more than one pinhole, in which case each pinhole projects a different view of the object onto the detector plane. Depending on the size of the object, the spacing between pinholes, and the system magnification (i.e., the relative position of the pinhole surface), the different pinhole projections of the object (i.e., the fields of view of the pinholes) can overlap on the detector plane. In such a case, a single detector element sees several different lines though the object, one though each pinhole, a condition referred to as overlapping, coding, or multiplexing. A pinhole aperture that causes such a condition is referred to as a multiple-pinhole coded aperture. This condition is illustrated in FIG. 4.

There are several other apertures that can be used to restrict the path of the gamma rays between the radioactive object and the detector in a tomographic imaging system. These apertures consist of fixed patterns such as annuli (see Walton, P. W., "An Aperture Imaging System with Instant Decoding and Tomographic Capabilities," Journal of Nuclear Medicine, 14(11):861-863, 1973; and Simpson, R. G., "Annular Coded-Aperture Imaging System for Nuclear Medicine," Ph.D. Dissertation, University of Arizona, Tucson, 1978) or Fresnel zone plates (Mertz, L. and N. O. Young, "Fresnel Transformation of Images," Proceedings of Intern. Conf. of Opt. Instrum., p. 305, 1961; Barrett, H. H., "Fresnel Zone Plate Imaging in Nuclear Medicine," Journal of Nuclear Medicine, 13(6):382-385, 1972; and Rogers, W. L. et al., "Application of a Fresnel Zone Plate to Gamma-Ray Imaging," Journal of Nuclear Medicine, 13(8):612-615, 1972). Other patterns are time-modulated, such as rotating slits (Tanaka, E. and T. A. Iinuma, "Image Processing for Coded Aperture Imaging and an Attempt at Rotating Slit Imaging," Proc. Int. Conf. Process. Scintigr. 4th, Orsay, pp. 43-45, 1975; and Miller, E., "Radially Symmetrical Coded Apertures," M. S. Thesis, University of Arizona, Tucson, 1978) and Fourier apertures (Mertz, L., "Applicability of the Rotation Collimator to Nuclear Medicine," Opt. Commun., 12:216, 1974; and Chou, C and H. H. Barrett, "Gamma-Ray Imaging in Fourier Space," Opt. Lett., 3(5):187-189, 1978).

Any of the above collimator designs may be used in either planar imaging or in SPECT. In SPECT a three dimensional radionuclide distribution can be mapped by collecting a data set that consists of many line integrals or planar integrals through the distribution. This is accomplished by using a combination of at least one detector with position sensing capability, at least one aperture and, usually, system motion to collect a data set consisting of many different projections of the distribution. A reconstruction algorithm is then used to estimate the activity distribution that most likely caused the measured data set. Many such algorithms have been developed and tailored to the particular aperture system by those skilled in the art in order to optimize the utilization of the information so gathered to produce the best possible image of the body under observation.

Figure 5:
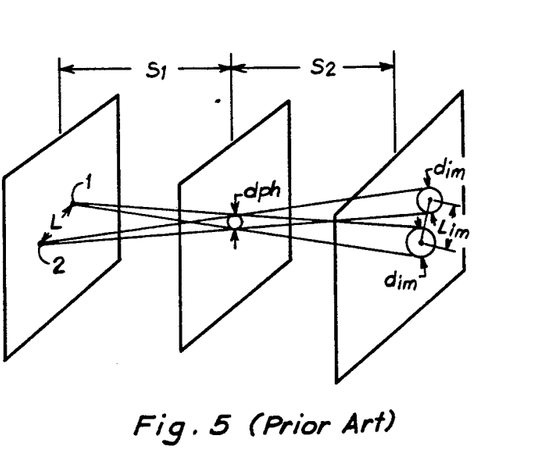
FIG. 5 is a schematic view demonstrating one definition of the spatial resolution of two separate points on the source plane as viewed at the detector plane through a finite-sized pinhole aperture.

One of the concerns in designing radiotracer-imaging apparatus is the spatial resolution corresponding to the various aperture systems used in conjunction with a gamma-ray detector. One generally accepted definition of spatial resolution having a simple mathematical form is the minimum resolvable spacing, as a result of the finite dimension of the aperture, between two points at the source of radiation. For example consider the pinhole aperture illustrated in FIG. 5. For a single pinhole aperture of diameter $d_{ph}$ on a plane located at a distance $s_1$ from the radioactive source and $s_2$ from the detector plane, each radioactive point at the source produces an image consisting of a collection of detected photons that define a circular region of diameter $d_{1m}$ on the detector plane. Two distinct points 1 and 2 separated by the distance L at the source are generally considered resolved by the imaging system if their separation is such that negligible overlap exists between the two corresponding circular images on the detector plane. Therefore, it is obvious that, as a general proposition, the spatial resolution of an imaging system using a certain aperture increases with the distance between the aperture surface and the detector surface. In mathematical terms, it is clear that $$d_{im} = d_{ph}(s_1 + s_2)/s_1$$

provided that the aperture surface is parallel to the detector surface. The separation of the two circular images requires that their centers be at least a distance equal to $d_{im}$ apart; that is, $$L_{im} = d_{ph}(s_1 + s_2)/s_1$$

Since the distance of the centers of the circular images is related to the distance L by the simple geometrical relationship $$L_{im} = L(s_2/s_1),$$

it follows that in order to obtain spatial resolution of points 1 and 2 in a tomographic system using a single pinhole aperture the two points must be separated by a distance L at least equal to $d_{ph}(s_1 + s_2)/s_2$. Thus, for a given pinhole aperture and detector resolution, the distance L is minimized (and therefore the spatial resolution of the system is optimized) by increasing the distance $s_2$ between the aperture and the detector surfaces.

Good spatial resolution is important for imaging systems because structural details in the object of a size that is smaller than the resolution will not be accurately reproduced in the image and in fact may not be visible at all. In a clinical image, object details are blurred on a scale equivalent to the spatial resolution; so, the effects of pathology smaller than this scale may not be detectable.

The scintillation camera is the state-of-the-art gamma-ray detector universally used in nuclear medicine. It consists of a crystal (sodium iodide) capable of producing scintillation (fluorescent light emission) at the point where struck by gamma-ray radiation. Multiple photomultiplier tubes are positioned in an array on the plane of the crystal to receive the light emitted by the scintillator, thus providing the means for recording each scintillation event and estimating its position on the plane. The detector resolution corresponds to the precision with which the center of the scintillation flash can be estimated using the array of photomultiplier tubes. Current technology permits the construction of scintillation cameras with detector resolution of the order of 3 mm. Many patents and much literature exists describing various implementations of nuclear imaging systems employing scintillation camera detectors. See, for example, U.S. Pat. No. 3,825,757 to Barrett et al. (1974), U.S. Pat. No. 3,961,191 to Stoner et al. (1976), U.S. Pat. No. 4,092,540 to Barrett (1978), and U.S. Pat. No. 4,514,632 to Barrett (1985). All of these patents disclose inventions designed to produce improved medical imaging systems using scintillation cameras.

Nearly all current SPECT systems use the motion of one or at most a few position-sensitive detectors to provide the various angular projections used for reconstructing the three-dimensional emission distribution. Such motion often results in artifacts in the reconstruction due to imperfectly controlled detector motion or inadvertent patient motion during the study. Dynamic studies involving radiotracer redistribution on timescales short with respect to the total acquisition time are not possible with such a SPECT system. A modular camera system with fixed cameras having different viewing angles, as described in U.S. Pat. No. 4,514,632 to Barrett (1985), does not have these drawbacks.

This invention is directed to a modular detector system having multiple-pinhole coded apertures for use in tomography. For such a system it is apparent that, for a given camera resolution and distance $S_1$ between the radioactive source and the aperture surface, spatial resolution increases with the distance $S_2$ between the aperture and the detector surfaces, as illustrated above. When overlapping of images occurs, there is an ambiguity about which pinhole was traversed by any gamma ray interacting in an overlapping region. This is usually resolved in the reconstruction step by postulating two gamma rays, one for each possible pinhole. Consequently, overlapping images result in additional, non-physical events that contribute to noise and to the possibility of artifacts in the reconstruction. Ideally, the detector surface would be placed only as far from the aperture surface as necessary to obtain an acceptable spatial resolution of the object under observation and avoid image overlapping. For fixed spatial resolution (fixed $S_2$) and fixed opening angle of the pinhole bore (usually chosen so that all or most of the object region of interest is visible), the condition that images not overlap fixes the number of possible pinholes in a given area of collimator. The quantum efficiency of the system and thus its sensitivity depends on the number of pinholes. Thus, for fixed system spatial resolution, using a detector with low resolution means that magnification must be used (i.e., large $S_2$); but this results in reduced system sensitivity (corresponding to the probability of detecting an emitted photon).

System sensitivity is important because the amount of radiotracer that can be administered to a patient is limited by the radiation dose that a patient can tolerate. Current scintillator-based SPECT systems, including modular scintillation camera systems, have detector resolutions of 0.3–0.5 cm, reconstructed voxel resolutions of 0.5–1.0 cm, and limited system sensitivity. For these systems, increasing the spatial resolution by increasing $S_2$ will increase image overlapping, increasing the noise and thereby decreasing the overall system sensitivity. Image overlapping may be reduced by decreasing the number of pinholes, but this also decreases system sensitivity. The number of photons emitted by a given voxel decreases as the cube of the linear voxel size and thus decreases as the cube of the spatial resolution. Many of the most important imaging tasks, such as tumor detection or brain imaging, are already photon starved when current scintillator-based SPECT systems are used with existing radiotracers. In this sense, the current scintillator-based SPECT technology may be said to have reached its spatial resolution limit.

Therefore, it would be very desirable to have a detector system for nuclear medicine applications that has higher spatial resolution, so that a SPECT system could be developed having both improved reconstructed resolution and the required sensitivity improvement needed to make its use practical. This invention relates to the use of a semiconductor detector in combination with multiple-pinhole coded apertures to produce such an improved tomographic imaging system.

Semiconductor detectors are based on a surface of semiconductor material with high atomic number that, as a result of gamma-ray absorption, produces hole-electron pairs (typically one pair for about 3 eV of energy absorbed). By applying an electric field across the semiconductor, a current results whenever gamma rays are absorbed by the semiconductor material, thus providing a means for detecting and measuring each radiation absorption event. By subdividing the area of the semiconductor surface into separate cells and by measuring the currents generated in each cell, the spatial distribution of the incident radiation can be determined. Because gamma rays incident on a semiconductor surface can be monitored electronically (rather than with photomultiplier technology), a subdivision of the detector surface into smaller individual sensor cells becomes feasible, with a higher detector resolution than achievable with scintillation camera crystals. Therefore, semiconductor detectors offer a vehicle for improved applications in tomographic imaging apparatus. The main problem associated with their utilization has been the difficulty in connecting and constructing electronics to read out the large number of sensor cells in the detector array.

For example, U.S. Pat. No. 4,879,464 to Iinuma (1989) describes a radiation imaging detector that consists of an array of semiconductor elements individually connected to a multiplicity of corresponding signal processing circuits. Because of this complex circuitry requirement, the detector of this invention is restricted by space constraints in the number and size of each individual sensor cell, thus also limiting the space resolution of the detector. Another possibility is to use a row-by-column readout technique, as described by Iwanczyk, J. S. et al., "Development of Mercuric Iodide Energy Dispersive X-Ray Array Detectors," IEEE Transactions on Nuclear Science, Vol. 35, No. 1, Feb. 1988, 93–97. Such an approach still requires too much additional electronics to be practical for reading out very large detector arrays, and the additional electronic noise resulting from cross-connecting so many detectors reduces the ability of the system to discriminate between gamma rays or different energy and thus to reject scattered gamma rays. Others, who have considered using integrated circuit techniques to construct the readout system directly on the detector, include Audet, S. A. and S. E. Wouters, "Monolithic Integration of a Nuclear Radiation Sensor and Transistors on High-Purity Silicon," IEEE Transactions on Nuclear Science, Vol. 37, No. 1, Feb. 1990, 15–20; and Cho., G. et al., "Assessment of TFT Amplifiers for a-Si:H PIXEL Particle Detectors," IEEE Transactions on Nuclear Science, Vol. 37, No. 3, June 1990, 1142–1148. However, these techniques require the use of silicon, which has far too low a detection efficiency for gamma rays of the energies used in medical applications.

An improved semiconductor detector having a separate detector array and integrated circuit readout system is illustrated by Gaalema for infrared sensing applications (see IEEE Transactions on Nuclear Science, Vol. NS-32, No. 1, February 1985, p. 417). The present invention uses semiconductor detector of the type described by Gaalema to sense emitted gamma-ray radiation in conjunction with apertures used in a tomographic apparatus. It is found that the combination makes it possible to increase both the spatial resolution and the system sensitivity making possible and practical a very high resolution SPECT imaging system.

BRIEF SUMMARY OF THE INVENTION

One objective of this invention is the development of tomographic apparatus with increased spatial resolution that would lend itself to compact sensor surface geometries for nuclear medicine applications.

Another objective of the invention is a tomographic apparatus that yields the desired level of spatial resolution with no overlapping or with greatly reduced overlapping, thus simplifying the complexity required for the corresponding reconstruction algorithm.

Another goal of the invention is a tomographic apparatus that has fixed detectors and a multiple pinhole coded aperture that would allow fully three-dimensional reconstruction without detector motion, so that high resolution dynamic tomography is possible without the kind of artifacts that the detector motion would otherwise produce.

A further goal of the invention is a tomographic apparatus that includes a semiconductor detector with a much larger number of sensor cells than possible with scintillation cameras, thus enabling the construction of a detector with greatly improved spatial resolution.

Still another objective of the invention is an apparatus that, as a result of the greater resolution of its detector, allows the use of a greater number of apertures in the aperture surface and thus has more system sensitivity and more viewing angles, both of which result in improved reconstruction of the object.

According to these and other objectives, the present invention consists of a hybrid semiconductor gamma-ray detector in combination with attenuating apertures of the kind used in emission computed tomography. The detector comprises a slab of semiconductor material partitioned into multiple cells individually connected to a multiplexer through indium-bump pressure welds for the sequential read-out of integrated pulses generated in each cell as a result of gamma-ray absorption events. The single output channel provided by the multiplexer permits the construction of semiconductor sensor cells approximately one half to one millimeter in size for improved spatial resolution of the detector. The greater resolution of the detector makes it possible to narrow the distance $S_2$ between the image-forming apertures and the detector's surface to no more than twice the minimum distance at which the fields of view of adjacent pinholes overlap, which reduces the size of the overall apparatus and is found to keep overlapping of the gamma-ray radiation to a minimum. As a result of the smaller acceptable distance between the aperture surface and the detector, it is also possible to have a greater number of apertures and thus better system sensitivity.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DETAILED DESCRIPTION OF THE INVENTION

The heart of this invention lies in the recognition that the use of a semiconductor detector provides a vehicle for great improvements in tomographic gamma-ray imaging systems. Therefore, a specially designed detector surface is disclosed in combination with attenuating aperture surfaces for three-dimensional imaging of gamma-ray radiation emitted from controlled radio nuclides.

Figure 6:
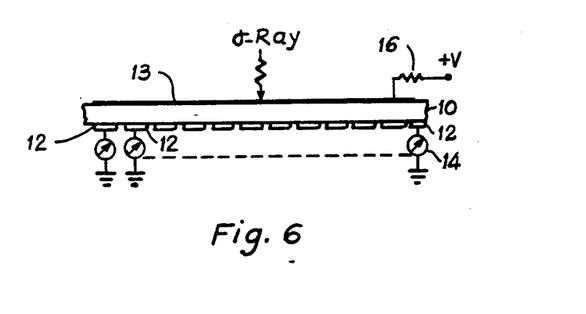
FIG. 6 is a schematic illustration showing in a simplified way the conceptual operation of a semiconductor sensor apparatus according to this invention.

The formation of hole-electron pairs as a result of the gamma-ray absorption of certain high atomic number semiconductor materials is exploited to provide the sensor surface of a gamma-ray detector. Referring to the drawings, wherein like parts are identified with like symbols and numerals throughout this specification, FIG. 6 illustrates the conceptual operation of a segmented semiconductor detector array showing in cross-sectional representation both sides of a slab 10 of semiconductor material coated with electrodes (12 and 13) for electrical connection with the material. The electrode 13 is a continuous plate attached to and covering the surface of the side of the slab receiving gamma-ray radiation, while the other side is partitioned into multiple cells by using separate read-out electrode pads 12 attached thereto, so that each pad corresponds to a well defined region of the slab. By applying an electric field to the electrodes through a resistor 16 and across the semiconductor material 10, the hole-electron pairs generated by incident photons due to gamma radiation contribute to a current that can be read out of each electron pad in the form of a pulse that can be registered and measured by individual meters 14. The meter 14 in FIG. 6 represents conceptually the more complex circuitry often referred to as event logic. An example of such circuitry might be a charge sensitive preamplifier capacitively coupled to the detector cell and in turn connected to a linear amplifier and various discriminators to select pulses by pulse height. Thus, in principle, by monitoring the current flow out of each cell, it is possible to determine the particular cells that have received gamma radiation because a pulse will be registered at the corresponding read-out electrodes. By subdividing the semiconductor slab into many individual cells (cells less than one half millimeter in nominal width are currently feasible), the spatial resolution capabilities of the detector surface are improved and the quality of the reconstructed image is correspondingly enhanced. Furthermore, because the height of the pulse registered is proportional to the energy deposited by the gamma-ray's interaction, the pulse height can also be used to differentiate between direct radiation, scattered radiation, and system noise. Typically, 3-5 eV are required to produce a hole-electron pair in a semiconductor slab and 100 to 300 keV gamma rays are used for tomographic purposes. Therefore, if, for example, 300 keV radiation is used, an incident gamma ray will produce about 100 thousand hole-electron pairs, which in turn yield a distinct current pulse easily distinguishable from the smaller pulses produced by scattered gamma rays and system noise. This high energy resolution feature of the semiconductor detector makes it possible to recognize and eliminate signals from scattered gamma rays, that would otherwise produce a low level background haze, and therefore also improve the quality of the resulting reconstructed image. The main problem with the physical implementation of this apparatus lies in the space and cost limitations underlying the separate circuitry required for measuring, amplifying, and transmitting the electrical signal produced at each electrode pad 12.

Figure 7:
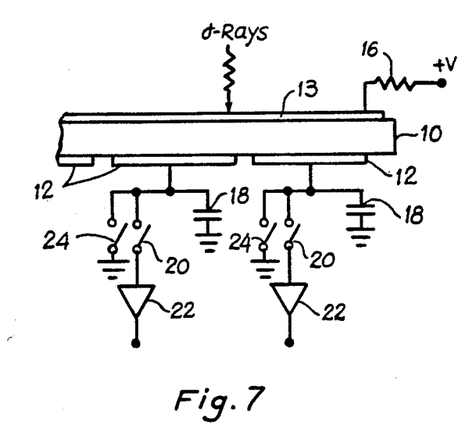
FIG. 7 shows in an enlarged partial representation the conceptual operation of a semiconductor sensor apparatus according to this invention, showing additional features related to storage, reset and signal amplification.

As illustrated in the enlarged partial representation of FIG. 7, rather than metering current pulses, the current out of each pad 12 is stored in a corresponding capacitor 18 connected to each pad and to ground. An output switch 20 is connected to each capacitor and to a signal amplifier 22, so that a voltage read-out (corresponding to the charge accumulated by the current to the capacitor) is signaled and amplified for each pad 12 when the corresponding switch 20 is closed. By sequentially closing all switches 20 at fixed intervals, a read-out is obtained for each pad (and correspondingly for each cell of the detector surface) of the voltage generated by the current through that cell during the interval. Accordingly, any voltage greater than that generated by the normal leakage currents for the semiconductor used (a known quantity) is measured and compared to the expected voltage resulting from the absorption of a gamma ray. If a match is registered for a given cell, within the tolerance acceptable for the system, it indicates that a gamma ray has been detected by that cell.

Figure 8:
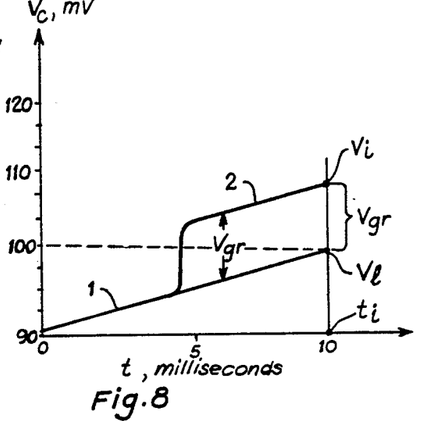
FIG. 8 is a typical time plot of the voltage output from a storage capacitor connected to the cell electrode of a semiconductor slab in response to gamma-ray absorption.

For example, FIG. 8 shows a typical case where 300 keV gamma rays are used with a semiconductor sensor requiring 5.2 eV for the formation of one hole-electron pair. Line 1 illustrates the typical increase in the voltage $V_c$ in each storage capacitor 18 due to leakage current as a function of time t for each ZnCdTe (zinc-cadmium-telluride) semiconductor cell subjected to a differential bias voltage. At the end of a fixed time interval $t_i$, the capacitor voltage will be equal to $V_1$ (leakage voltage) unless additional current through the cell has resulted from incident gamma radiation. As line 2 illustrates, each gamma ray absorbed by the cell connected to the particular pad being monitored generates 58 thousand hole-electron pairs (300 keV/5.2 eV), which in turn yield an approximately fixed voltage pulse $V_{gr}$ ($V_{gr2}$=9.2 mV if capacitor 18 is 1.0 pf) that is directly reflected as an increase over the normal leakage voltage $V_1$, for a total voltage $V_i$ accumulated during the time interval $t_i$. For ZnCdTe cells of size 0.5 mm $\times$0.5 mm $\times$2.0 mm, 200 V bias, a capacitor 18 of 1.0 pf and an integration time of 10 milliseconds, $V_1$=100 mV. Of course, the specific values vary with the type of semiconductor material used, but remain constant for a given material and given operating conditions. In particular, most semiconductor detectors exhibit some charge carrier trapping which is dependent on the quality of the detector crystal, the operating voltage and the depth of interaction of the gamma ray in the detector crystal. Here, for simplicity we assume complete charge collection. Thus, if $V_c$ for a cell is approximately equal to $V_i$, it is a clear indication that a gamma-ray absorption event has occurred in the particular cell; if $V_c$ is not approximately equal to $V_i$, either no event has occurred or only events of scattered gamma-ray absorption or of background noise have occurred. Since the time interval used is very small (of the order of 10 milliseconds), the probability that more than one gamma ray is absorbed during each interval is minimal and decreases with the surface size of each cell. For 0.25 mm$^2$ cells, and a read-out time of 10 milliseconds, a radiation flux of less than 1 photon per 10 milliseconds per square millimeter (that is, 100 photons/sec-mm$^2$) is required in order to avoid excessive rejections based on multiple gamma-ray absorption. Given the parameters of operation for tomographic systems, this requirement is easy to meet. Moreover, it corresponds to a rate limitation nearly 100 times higher, i.e. better, than for conventional scintillator cameras. Therefore, only measurements of $V_c$ approximately equal to $V_i$ are considered significant and all others are discarded from the data utilized for image reconstruction analysis. This approach should yield an energy resolution close to the limiting value for the detector material, which for most semiconductor detectors is of the order of a few percent, considerably better than the 10 percent energy resolution achievable with scintillation crystal apparatus. By sequentially sampling each capacitor 18 at each time interval, a complete read-out is obtained of the spatial distribution of all gamma-ray absorption in the semiconductor slab 10 during that interval. All capacitors are then sequentially discharged to ground (immediately after read-out) through a corresponding reset switch 24, and the cycle is repeated for the next time interval.

It is noted that prior art gamma-ray sensing apparatus, whether based on scintillation crystal or semiconductor technology, is based on the detection of instantaneous pulses corresponding to each event of an incident gamma ray. By virtue of the utilization of storage capacitors, the present invention is based on the measurement of the integrated value of such pulses over a given time interval. The interaction of a gamma ray with semiconductor material does not initiate the read-out process, as is done in most prior art gamma-ray detectors. Rather, the detector functions as a passive integrator. It is believed that the relatively long integration times possible with this apparatus (of the order of 10 milliseconds) will result in improved energy resolution because of the improved charge collection.

Figure 9:
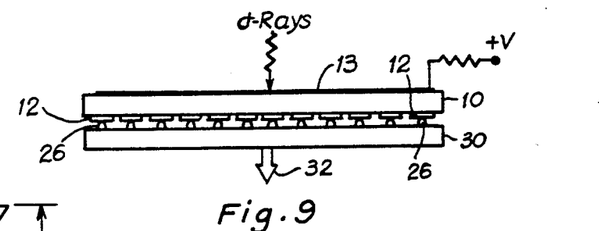
FIG. 9 is a cross-sectional schematic representation of the functional combination of a semiconductor slab sensor with a multiplexer through indium pump cold welds.
Figure 10:
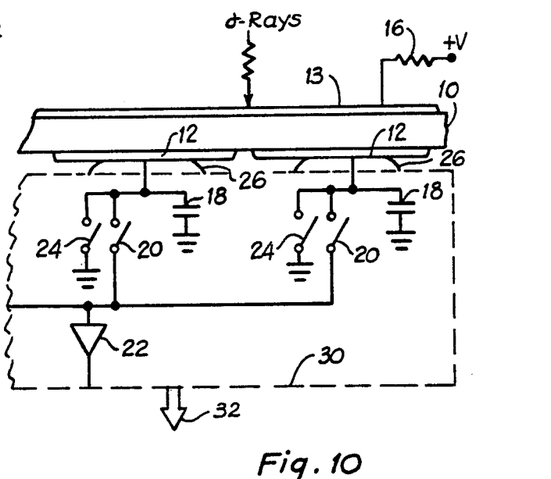
FIG. 10 is an enlarged partial representation corresponding to FIG. 7 illustrating the equivalent circuitry of a multiplexer replacing individual output channel circuitry.

As mentioned above, the main problem with the utilization of semiconductor sensors in gamma-ray detection is the difficulty of providing a separate electronic output channel for each cell. So long as the total number of cells is relatively small, it is possible to construct switching circuitry to implement the read-out function illustrated by the apparatus of FIG. 7, but the task becomes practically impossible when relatively large numbers of cells are contemplated. Since large arrays of small individual cells are necessary for greater spatial resolution and correspondingly for better image quality and counting efficiency, the ability to construct a very large array (30×30) of small sensor cells (less than 1.0 mm$_2$) is very desirable. A few hundred such arrays would be required for a multiple pinhole array SPECT system. Providing readout for such large arrays is accomplished by coupling the semiconductor slab illustrated in FIGS. 6 and 7 with a multiplexer device of the type developed for infrared detection apparatus. These devices consist of an electronic array of switches that are closed and reset sequentially, so as to sequentially connect the channel corresponding to each switch to a common output channel. FIG. 9 is a cross-sectional schematic representation of the functional combination of the semiconductor slab 10 with a multiplexer 30 and a common output channel 32. Because of their monolithic construction, these multiplexers are very small and can easily be pressure coupled to the electrode pads 12 of the semiconductor slab 10 by means of indium bump cold welding, a process well known to those skilled in the art. Multiplexers are available commercially from the Hughes Company of Carlsbad, Calif.; the Litton Company of Tempe, Ariz.; the Rockwell Company of Los Angeles, Calif.; and others. However, commercial multiplexers are usually of a size that is smaller than is optimal for this approach unless an expansion coupler is used. The hybrid combination of the semiconductor slab with the multiplexer through individual indium bumps 26 connected to each electrode pad 12 is illustrated in FIG. 9. FIG. 10 is an enlarged partial representation corresponding to FIG. 7 wherein a multiplexer is used instead of individual output channel circuitry. The multiplexer's equivalent circuitry shown in the figure illustrates the common output channel 32 connected to each semiconductor cell through a corresponding output switch 20. It should be mentioned that many of the components shown in the equivalent circuit of FIG. 9 correspond to active components in the multiplexer integrated circuit. For instance, the holding capacitor 18 usually corresponds to the base to drain capacitance of a field effect transistor (FET) and switches 20 and 24 correspond to other FET's.

In the selection of semiconductor material for the sensor apparatus herein described, it is important that leakage currents be minimized. To that end, it may be necessary to lower the operating temperature of the device by using a thermo-electric cooler to reduce the leakage current of the semiconductor to acceptable levels. A temperature reduction of about 50 degrees Fahrenheit was found to be adequate for CdTe (cadmium-telluride) material. By using a new material, ZnCdTe, it is found that no temperature reduction is necessary because of its distinctly greater insulating characteristics and correspondingly lower leakage currents. The material is also particularly suitable for large sensor surface construction (in the order of 2 to 6 cm wide) in 0.5 to 5 mm thick slabs, which is the required thickness for gamma-ray absorption.

Figure 11:
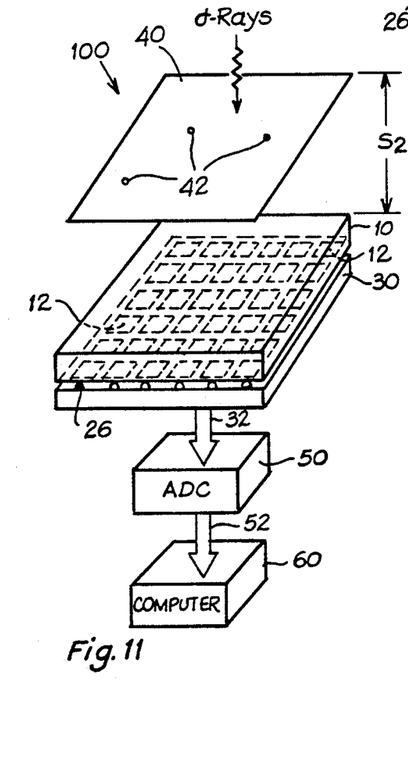
FIG. 11 is a diagrammatic perspective view of a gamma-ray tomographic imaging system that combines a pinhole aperture array with a semiconductor detector slab and a multiplexer.

FIG. 11 represents a diagrammatic perspective view of a gamma-ray tomographic imaging system 100 that combines a pinhole aperture array with a semiconductor detector slab 10 and a multiplexer 30. The attenuating surface 40 (which is not necessarily planar, as illustrated in the figures) contains apertures in the form of individual pinholes 42 appropriately positioned in the surface to produce the desired field of view on the parallel top surface of the semiconductor sensor 10 (coated with the electrode 14, not shown in FIG. 11) located at a distance $S_2$ apart. As mentioned above, the distance $S_2$ is preferably selected so as to eliminate overlapping of the image information received by the electrode surface 14. It is found that overlapping is kept to a minimum when the distance between the aperture plane and the detector is no more than twice the minimum distance at which the fields of view of adjacent pinholes begin to overlap. It is noted that pinhole apertures are shown here for illustration, but any other gamma-ray image-forming optical device could be similarly combined with the semiconductor detector to practice the invention. As explained above, the sensor for the gamma-ray imaging detector consists of the slab 10 of a semiconductor material capable of absorbing the gamma-ray radiation received from a source through the image forming apertures. The semiconductor slab is divided into an array of detector cells by a grid of separate electrode pads 12 on the bottom surface of the slab connected to the multiplexer integrated circuit 30 for accumulation of the electric pulse generated at each pad and read-out of the corresponding voltage under control of a computer 60. The analog output 32 of the multiplexer is digitized in an analog-to-digital converter 50 and the resulting signals 52 are transmitted to the computer 60 for input to the reconstruction algorithm and display of the resulting image. This embodiment of the invention envisions a multiplexer circuit having similar cell spacing to that of the detector array (0.5–1.0 millimeter). Therefore, a large detector array (e.g., 30×30) would require a multiplexer somewhat larger than conventional integrated-circuit multiplexers. The yield problems commonly encountered in producing large area integrated circuits are not expected to occur in a large multiplexer because the active area of the circuit covers only a tiny fraction of the silicon surface (i.e., the multiplexer has a space geometry).

Figure 12:
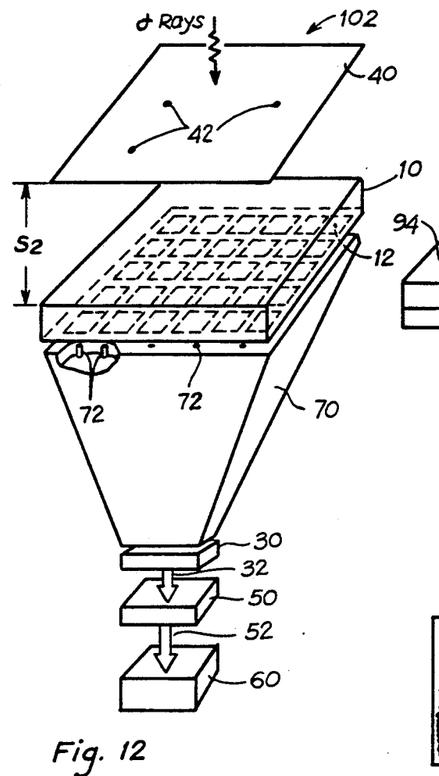
FIG. 12 is a diagrammatic perspective view of another embodiment of a gamma-ray tomographic imaging system that combines a pinhole aperture array with a semiconductor detector slab, an expansion coupler, and a multiplexer.

Multiplexers of the kind required for this invention are normally manufactured for infrared sensing apparatus, which requires a spatial resolution (cell size) in the order of a few tens of microns. Therefore, off-the-shelf multiplexing devices are normally smaller than required for indium-bump connection with gamma-ray semiconductor detectors, which will have cell sizes of 0.5–1.0 millimeters. In order to permit the utilization of off-the-shelf devices, an alternative embodiment 102 of the invention incorporates an expansion coupler between the semiconductor sensor layer and the multiplexer, as shown in FIG. 12. An expansion coupler 70 would permit the connection of a larger gamma-ray semiconductor sensor 10 with the smaller active area of the multiplexer 30 through individual conductive paths 72 coupling each semiconductor electrode pad 12 with a corresponding indium-bump connection on the surface of the multiplexer (not seen in FIG. 12). The expansion coupler illustrated in the figure can be assembled using Z-plane technology. First, conductive lines are laid down on a silicon or ceramic substrate by photolithographic techniques. Then the substrate is thinned by lapping or grinding on the end of the wafers where the conductive line spacing is to be closest. The coupler is then assembled by putting the wafers together into a prism so that there are arrays of conductive lines with different spacing on the front and back surfaces. The array spacing on the small end may be fine tuned by lapping the surface at an appropriate angle and by specifying the size and shape of the indium bumps via a photolithographic mask.

Figure 13A:
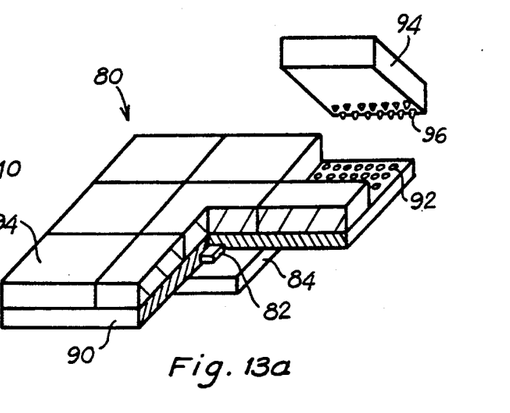
FIGS. 13a and 13b show a design for a two-stage "flat" expansion coupler using both silicon photolithography construction and PC-board techniques.
Figures 13B, 13C, 13D:
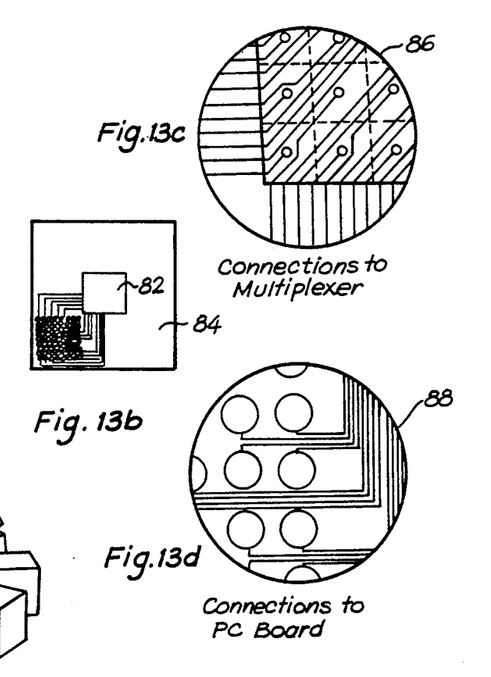
FIGS. 13c and 13d illustrate in enlarged view patterns of conductor-wire connections to the multiplexer and to the PC board, respectively.

A similar embodiment of the invention can be obtained using a two-stage "flat" expansion coupler. FIGS. 13a and 13b show a design for such a flat coupler 80 using both silicon photolithography construction and PC-board or thick film hybrid circuit techniques. Obviously, an imaging system using the flat coupler would be substantially more compact than that of FIG. 12. The design for a flat expansion coupler uses two stages. The first stage utilizes a multiplexer 82 face down on a silicon chip 84. The pattern of conductor wires 86 illustrated in the enlarged views of FIGS. 13c and 13d is made on the surface of the silicon chip 84 by photolithography. Connection to the multiplexer is by indium-bump bonding (not shown in the figures), through soft-metal bumps laid down by photolithography. The second stage is very similar to the first stage pattern, but uses multi-layer PC-board or thick film hybrid circuit techniques. Connection to the first stage is by indium bumps (also not shown) to the silicon chip 84 with the pattern 88 on the bottom side of the PC board 90. Plated-through holes 92 connect to the top side of the PC board to which detector pads 94 are connected via indium bumps 96.

Figure 14:
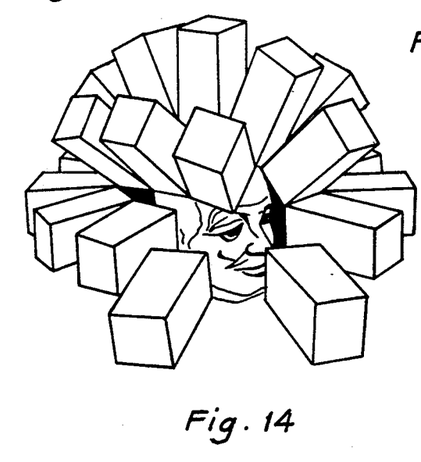
FIG. 14 illustrates, in diagrammatic perspective, a gamma-ray tomographic imaging system incorporating the electronic detector and multiple-pinhole coded aperture combination of this invention in a hemispherical configuration suitable for brain imaging.

In equivalent embodiments of the invention, the described detectors (in any of the configurations of FIGS. 11, 12 or 13) may be combined with different imaging aperture geometries according to the particular requirements of the imaging system. FIG. 14, for example, illustrates a system incorporating the combination of the electronic detector and multiple-pinhole coded aperture of this invention in a hemispherical configuration. Although not visible in the figure, each detector module is equipped with a multiple-pinhole coded aperture, and no motion of the modules or apertures is required. Because of the high resolution of modular cameras based on semiconductor detectors used in combination with coded apertures, this geometry is particularly suitable for a stationary apparatus for tomographic brain imaging.

It is expected that the imaging system described in this specification will have a number of other of practical uses. With an appropriate coded aperture system, as would be obvious to those skilled in the art, it could form the basis of a high-resolution, surgical-imaging probe that should improve the ability to detect small tumors labelled with a tumor seeking radiotracer, such as radiolabeled monoclonal antibody. Another example of a nuclear medicine application would be as part of a high-resolution, spot-imaging camera. Trade-offs in collimator design make such systems most practical for imaging targets that have high activity per unit volume and are at shallow depths. Examples include lymphoscintigraphy of the peripheral lymphatics and thyroid scanning.

A high-resolution imaging system making use of the device shown herein would also be very valuable for imaging the distribution of gamma-emitting radiotracers in small experimental animals. Existing gamma-ray cameras have a spatial resolution which is too poor to be useful in imaging small animals. Consequently, the usual approach is to study a large number of animals simultaneously. A few animals are sacrificed at each stage of the study, the organs are removed, and their activities are counted in a well counter. High resolution imaging would allow longitudinal study of individual animals, reducing error due to inter-animal variation and conserving animals. Another application could be in a portable, high-resolution, detector capable of simultaneously imaging and spectroscopy for the nuclear industry or astronomy.

It is also anticipated that this invention will have great utility in the development of stationary dynamic imaging systems. As a result of the higher spatial resolution of the detector, the distance between a multiple-pinhole coded aperture and the detector surface can be minimized, thus permitting a larger number of pinholes to be used without image overlapping, consequently greatly improving system sensitivity. A shorter $S_2$ will also result in a more compact design which is more convenient for clinical use. In addition, since an image can be reconstructed from data collected over a single, very short, time interval, the dynamic evolution of the observed subject can be monitored by the sequence of images so produced.

It is important to note that, for a multiple pinhole aperture and system of the type described herein, improving the spatial resolution of the detector makes it possible to increase the number of pinholes while keeping the degree of image overlap negligible or small (that is, by decreasing $S_2$, the aperture to detector distance). Thus, spatial resolution and sensitivity (counting efficiency) can be simultaneously improved. This is highly counter-intuitive and a very important result. Usually collimator systems trade off sensitivity against resolution; i.e., more spatial resolution means less sensitivity. This a very disadvantageous situation because the number of emitted gamma rays is approximately proportional to the volume of the voxel (that is, it goes down as the cube of its size). With existing collimator systems and low resolution (scintillator) detectors, high resolution can be obtained only by magnification (large $S_2$), thus with few pinholes and low sensitivity. By contrast, the approach of this invention allows us to increase the number of pinholes as we increase detector resolution and make $S_2$ smaller, so that sensitivity actually increases fast enough to nearly offset the volume (voxel) decrease.

While the invention is described herein preferentially in terms of zinc-cadmium-telluride, any semiconductor material suitable for radiation detection, such as cadmium telluride, mercuric iodide, lead iodide, germanium, or thallium bromide, may be used with appropriate temperature control adjustments, if necessary.

Various other changes in the details, steps and materials that have been described may be made by those skilled in the art within the principles and scope of the invention herein illustrated and defined in the appended claims. Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

What we claim is:

1. A gamma-ray imaging apparatus for single-photon emission computed tomographic applications comprising, in combination:
   (a) an aperture imaging system, consisting of a multiple-pinhole aperture in a layer of radiation attenuating material, for providing a field of view through said multiple pinhole aperture;
   (b) a slab of semiconductor material positioned to receive gamma rays from a gamma-ray emitting source in said field of view and capable of absorbing incident gamma rays, wherein said slab of semiconductor material is subjected to an electric field between an electrode attached to the side of the slab exposed to radiation and a plurality of electrodes attached to the other side of the slab, whereby the slab is partitioned into a corresponding plurality of sensor cells individually capable of producing an electric current pulse when a gamma ray is absorbed within the cell;
   (c) a monolithic multiplexer coupled to said plurality of electrodes for the sequential rad-out of electric pulses generated in each of said sensor cells as a result of gamma-ray absorption events, wherein during each cycle of operation of the multiplexer the current-pulse output of each cell is integrated by accumulation in a corresponding capacitor means that is sequentially discharged producing a voltage signal through a single-output channel of the multiplexer and that is then reset for charging during the next cycle of operation; and
   (d) data processing means, coupled to said single-output channel of the multiplexer, for analyzing the voltage signals produced at said single-output channel and for constructing an image corresponding to the gamma-ray emitting source;
   wherein said slab of semiconductor material and said monolithic multiplexer constitute a single gamma-ray detector module.

2. The apparatus described in claim 1, wherein said monolithic multiplexer is coupled to said plurality of electrodes by means of indium-bump cold welds.

3. The apparatus described in claim 1, wherein said data processing means consists of an analog-to-digital converter for converting the analog voltage signal produced at said single-output channel of the multiplexer to a corresponding digital signal, and of a computer connected to the output of said converter.

4. The apparatus described in claim 1, wherein said semiconductor material is zinc-cadmium-telluride.

5. The apparatus described in claim 4, wherein said slab consists of a square approximately 2 to 6 cm wide and between 0.5 and 5 mm thick, said square containing a plurality of cells each approximately 0.25 $mm^2$; wherein said cycle of operation is repeated every 10 milliseconds; and wherein said gamma rays from a gamma-ray emitting source are emitted with a radiation flux of less than 1 photon per 10 milliseconds per square millimeter.

6. The apparatus described in claim 1, further comprising an expansion coupler between said plurality of electrodes and said monolithic multiplexer.

7. A gamma-ray imaging apparatus for single-photon emission computed tomographic applications comprising, in combination:
   (a) an aperture imaging system, consisting of a multiple-pinhole aperture in a layer of radiation attenuating material, for providing a field of view through said multiple pinhole aperture;
   (b) a slab of semiconductor material positioned to receive gamma rays from a gamma-ray emitting source in said field of view and capable of absorbing incident gamma rays, wherein said slab of semiconductor material is subjected to an electric field between an electrode attached to the side of the slab exposed to radiation and a plurality of electrodes attached to the other side of the slab, whereby the slab is partitioned into a corresponding plurality of sensor cells individually capable of producing an electric current pulse when a gamma ray is absorbed within the cell;
   (c) a monolithic multiplexer coupled to said plurality of electrodes for the sequential read-out of electric pulses generated in each of said sensor cells as a result of gamma-ray absorption events, wherein during each cycle of operation of the multiplexer the current-pulse output of each cell is integrated by accumulation in a corresponding capacitor means that is sequentially discharged producing a voltage signal through a single-output channel of the multiplexer and that is then reset for charging during the next cycle of operation; and
   (d) data processing means, coupled to said single-output channel of the multiplexer, for analyzing the voltage signals produced at said single-output channel and for constructing an image corresponding to the gamma-ray emitting source;
   wherein said slab of semiconductor material and said monolithic multiplexer constitute a single gamma-ray detector module; and
   wherein the distance between said multiple-pinhole aperture and said slab of semiconductor material is no more than twice the minimum distance at which the fields of view of adjacent pinholes overlap.

8. The apparatus described in claim 7, wherein said multiple-pinhole aperture imaging system consists of a hemispherical surface and wherein a multiplicity of said gamma-ray detector modules are positioned in hemispherical configuration around said hemispherical surface.

9. The apparatus described in claim 8, wherein said hemispherical surface is stationary.

10. A method for detecting gamma rays emitted from a source containing radionuclides and for reconstructing a corresponding image through computer analysis and data processing for single-photon emission computed tomographic applications, comprising the following steps:
   (a) exposing a gamma-ray emitting source to an aperture imaging system consisting of a multiple-pinhole aperture in a layer of radiation attenuating material;
   (b) positioning a slab of semiconductor material in the field of view of said multiple-pinhole aperture imaging system to receive gamma rays from the gamma-ray emitting source in said field of view, said semiconductor material being capable of absorbing incident gamma rays;

(c) subjecting said slab of semiconductor material to an electric field between an electrode attached to the side of the slab exposed to radiation and a plurality of electrodes attached to the other side of the slab, whereby the slab is partitioned into a corresponding plurality of sensor cells individually capable of producing an electric current pulse when a gamma ray is absorbed within the cell;

(d) coupling a monolithic multiplexer to said plurality of electrodes for the sequential read-out of electric pulses generated in each of said sensor cells as a result of gamma-ray absorption events;

(e) integrating the current-pulse output of each cell during each cycle of operation of said monolithic multiplexer by accumulation in a corresponding capacitor means that is sequentially discharged producing a voltage signal through a single-output channel of the multiplexer and that is then reset for charging during the next cycle of operation; and (f) coupling said single-output channel of the multiplexer to data processing means for analyzing the voltage signals produced at said single-output channel and for constructing an image corresponding to the gamma-ray emitting source;

wherein said slab of semiconductor material and said monolithic multiplexer constitute a single gamma-ray detector module; and wherein the distance between said multiple-pinhole aperture and said slab of semiconductor material is no more than twice the minimum distance at which the fields of view of adjacent pinholes overlap.

11. The method described in claim 10, wherein said monolithic multiplexer is coupled to said plurality of electrodes by means of indium-bump cold welds.

12. The method described in claim 10, wherein said data processing means consists of an analog-to-digital converter for converting the analog voltage signal produced at said single-output channel of the multiplexer to a corresponding digital signal, and of a computer connected to the output of said converter.

13. The method described in claim 10, wherein said semiconductor material is zinc-cadmium-telluride.

14. The method described in claim 13, wherein said slab consists of a square approximately 2 to 6 cm wide and between 0.5 and 5 mm thick, said square containing a plurality of cells each approximately 0.25 mm$^2$; wherein said cycle of operation is repeated every 10 milliseconds; and wherein said gamma rays from a gamma-ray emitting source are emitted with a radiation flux of less than 1 photon per 10 milliseconds per square millimeter.

15. The method described in claim 10, wherein said multiple-pinhole aperture imaging system consists of a hemispherical surface and wherein a multiplicity of said gamma-ray detector modules are positioned in hemispherical configuration around said hemispherical surface.

16. The method described in claim 15, wherein said hemispherical surface is stationary.

17. The method described in claim 10, further comprising the step of using an expansion coupler between said plurality of electrodes and said monolithic multiplexer.

* * * * *